United States Patent
Du

(10) Patent No.: US 9,040,579 B2
(45) Date of Patent: May 26, 2015

(54) COMBINATION THERAPY USING COENZYME Q10 AND A CAFFEIC ACID-DERIVED ESTER

(75) Inventor: Yansheng Du, Carmel, IN (US)

(73) Assignee: Chemigen, Indianapolis, IN (US)

( * ) Notice: Subject to any disclaimer, the term of this patent is extended or adjusted under 35 U.S.C. 154(b) by 498 days.

(21) Appl. No.: 13/275,661

(22) Filed: Oct. 18, 2011

(65) Prior Publication Data

US 2012/0100122 A1 Apr. 26, 2012

Related U.S. Application Data

(60) Provisional application No. 61/394,137, filed on Oct. 18, 2010.

(51) Int. Cl.
| | |
|---|---|
| *A61K 31/216* | (2006.01) |
| *A61K 31/122* | (2006.01) |
| *A61K 31/341* | (2006.01) |
| *A61K 31/355* | (2006.01) |
| *A61K 31/4406* | (2006.01) |
| *A61K 31/525* | (2006.01) |
| *A61K 38/44* | (2006.01) |
| *A61K 45/06* | (2006.01) |

(52) U.S. Cl.
CPC ............ *A61K 31/122* (2013.01); *A61K 31/216* (2013.01); *A61K 31/341* (2013.01); *A61K 31/355* (2013.01); *A61K 31/4406* (2013.01); *A61K 31/525* (2013.01); *A61K 38/44* (2013.01); *A61K 38/446* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2003/0139458 A1 * | 7/2003 | Du et al. ................ | 514/357 |
| 2003/0158237 A1 | 8/2003 | Saragovi et al. | |
| 2007/0232668 A1 | 10/2007 | Priebe et al. | |
| 2010/0160433 A1 | 6/2010 | Du et al. | |

FOREIGN PATENT DOCUMENTS

| | | |
|---|---|---|
| WO | WO-03/053425 | 7/2003 |
| WO | WO-2004/075883 | 9/2004 |

OTHER PUBLICATIONS

Mancuso, M., et al. "Coenzyme Q10 in Neuromuscular and Neurodegenerative Disorders" Current Drug Targets. Jan. 2010, 11(1), pp. 111-121.
Mancuso, Michaelangelo, et al. "Coenzyme Q10 and Neurological Disease" Pharmaceuticals, 2009, 2(3), pp. 134-149.
"Redox" Wikipedia, the free encyclopedia,2012, pp. 1-10.
"Coenzyme Q10" Wikipedia, the free encyclopedia, 2012, pp. 1-16.
"Semiquinone" Wikipedia, the free encyclopedia, 2012, p. 1.
Kaufmann, et al., "Phase II trial of CoQ10 for ALS finds insufficient evidence to justify phase III", Annals of Neurology, vol. 66, No. 2, Aug. 2009.
Liu, et al., "Evolution of Study on Prenentment and Amelipoate Parkinson's Disease by Nutrients" Journal of Anhui Agri. Sci. 2006, 34(11) Abstract Only.

* cited by examiner

*Primary Examiner* — Bong-Sook Baek
(74) *Attorney, Agent, or Firm* — Cesari and McKenna, LLP

(57) ABSTRACT

A pharmaceutical composition containing a mitochondrial electron transport chain enhancer (or an antioxidant) and a compound of formula (I) shown in the specification. This pharmaceutical composition can be used to treat neurodegenerative disorders.

4 Claims, No Drawings

COMBINATION THERAPY USING COENZYME Q10 AND A CAFFEIC ACID-DERIVED ESTER

CROSS REFERENCE TO RELATED APPLICATIONS

This application claims priority to U.S. Provisional Application Ser. No. 61/394,137, filed Oct. 18, 2010. The contents of the prior application are hereby incorporated by reference in their entireties.

BACKGROUND OF THE INVENTION

Neuronal loss is involved in neurodegenerative disorders such as Parkinson's disease, Huntington's disease, Alzheimer's disease, amyothrophic lateral sclerosis, and multiple sclerosis, stroke, and hearing loss. None of the drugs currently available is satisfactory in treating these disorders or even in slowing their progression. Some even produce undesirable side effects, such as motor fluctuations and dyskinesias in Parkinson's disease. See, e.g., Quinn, et al., Neurology, 1998, 51, S25-29.

Thus, there is an urgent need to develop effective neuroprotective drugs.

SUMMARY OF THE INVENTION

The present invention is based on a discovery that combined use of a mitochondrial electron transport chain enhancer (or an antioxidant) and caffeic acid phenethyl ester exhibits synergistic effect in treating neurodegenerative disease.

One aspect of this invention relates to a method of treating neurodegenerative disorders with an effective amount of a mitochondrial electron transport chain enhancer (or an antioxidant) and an effective amount of a compound of Formula (I):

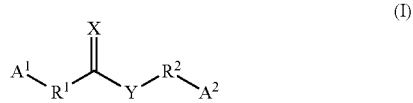

in which each of $R^1$ and $R^2$, independently, is $C_{1-8}$ alkylene, $C_{2-8}$ alkenylene, or deleted; each of $A^1$ and $A^2$, independently, is aryl or heteroaryl, optionally substituted with halogen, —CN, —$NO_2$, —OH, —SH, —$OR^a$, —$SR^a$, —$R^a$, —$R^a$—$OR^b$, —C(O)$R^a$, —S(O)$R^a$, —S(O)$_2R^a$, —$NR^bR^c$, —C(O)$OR^b$, —C(O)$NR^bR^c$, —O(O)$CR^b$, or —$NR^b$(O)$CR^c$, and each of X and Y, independently, is O, S, or $NR^d$, wherein each $R^a$, independently, is $C_{1-4}$ alkyl, and each of $R^b$, $R^c$, and $R^d$, independently, is H or $C_{1-4}$ alkyl.

The term "mitochondrial electron transport chain enhancer" refers to either a cofactor participating in the mitochondrial electron transport chain or a precursor of such a cofactor. Examples include, but are not limited to, Coenzyme Q10, vitamin C, riboflavin, niacinmide, and vitamin E.

The term "antioxidant" refers to a molecule that is capable of inhibiting the oxidation of other molecules and has no or litter harm to human. Examples includes, but are not limited to, Coenzyme Q10 (in any of the following three states: fully oxidized, i.e., ubiquinone; partially reduced, i.e., semiquinone or ubisemiquinone; and fully reduced, i.e., ubiquinol), thiol, ascorbbic acid, polyphenol, glutathione, vitamin C, vitamin E, catalase, superoxide dismutase, and peroxidase.

The term "alkyl" refers to a monovalent straight-chain or branched hydrocarbon radical, e.g., —$CH_3$, —$CH_2CH_2CH_3$, or —CH($CH_3$)$_2$. The term "alkylene" refers to a divalent straight-chain or branched hydrocarbon radical, e.g., —$CH_2$—, —$CH_2CH_2$—, or —$CH_2CH(CH_3)$—$CH_3$. The term "alkenylene" refers to a divalent straight-chain or branched hydrocarbon radical, containing one or more double bonds, e.g., —$CH_2CH$=CH—, or —$CH_2CH(CH_3)$CH=CH—$CH_2$—. The term "aryl" refers to a 6 to 12-carbon monocyclic or multicyclic (fused or separated) aromatic system wherein up to 4 atoms of each ring may be substituted. Examples of aryl groups include phenyl and naphthyl. The term "heteroaryl" refers to an aromatic 5-8 membered monocyclic, 8-12 membered bicyclic, or 11-14 membered tricyclic ring system, which contains 1-3 heteroatoms if monocyclic, 1-6 heteroatoms if bicyclic, or 1-9 heteroatoms if tricyclic (each heteroatom being O, N, or S). Examples of heteroaryl groups include pyridyl, furyl, imidazolyl, benzimidazolyl, pyrimidinyl, quinolinyl, indolyl, and thiazolyl.

Referring to the compound of Formula (I), $A^1$ can be aryl (i.e., phenyl, optionally substituted with halogen, —CN, —$NO_2$, —OH, —SH, —$OR^a$, —$SR^a$, —$R^a$, —$R^a$—$OR^b$, or —$NR^bR^c$), $R^1$ can be $C_{2-8}$ alkenylene, $R^2$ can be $C_{1-8}$ alkylene or $C_{2-8}$ alkenylene, and each of X and Y is O.

In one embodiment, $C_{2-4}$ alkenylene, $R^2$ is $C_{1-4}$ alkylene, and $A^2$ is phenyl optionally substituted with halogen, —CN, —OH, —SH, —$OR^a$, —$SR^a$, —$R^a$, —$R^a$—$OR^b$, or —$NR^bR^c$.

The compounds described above also include their salts and prodrugs, if applicable. Such salts, for example, can be formed between a positively charged substituent (e.g., amino) in a compound described and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) in a compound described above can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing compounds described above.

Shown below are exemplary compounds:

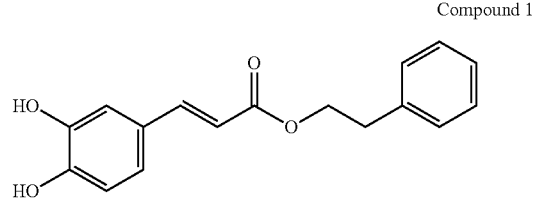

Compound 1

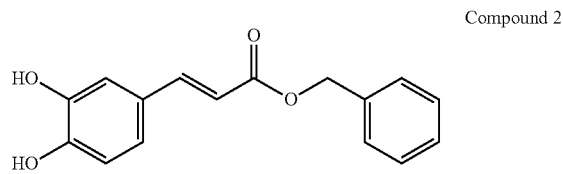

Compound 2

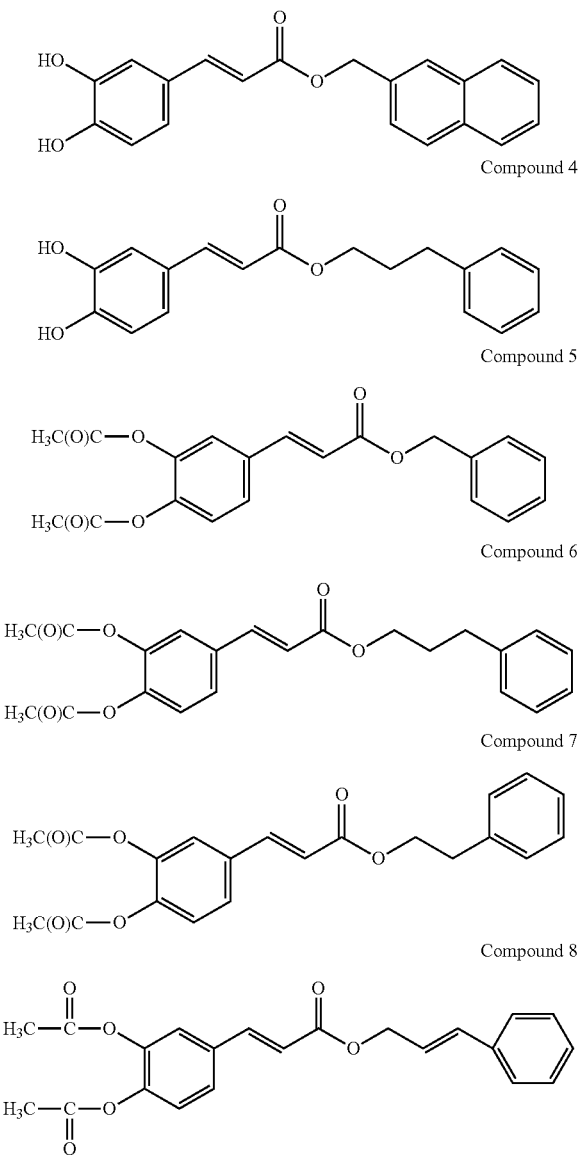

Another aspect of this invention relates to a pharmaceutical composition, which contains an effective amount of a mitochondrial electron transport chain enhancer (or an antioxidant) and an effective amount of a compound of Formula (I).

Also within the scope of this invention are the above-described composition for use in treating a neurodegenerative disorder, and the use of such a composition for manufacture of a medicament for the just-mentioned treatment.

The details of an embodiment of the invention are set forth in the description below. Other features, objects, and advantages of the invention will be apparent from the description and the claims.

DETAILED DESCRIPTION OF THE INVENTION

The compounds of formula (I) used to practice this invention can be synthesized by methods well known in the art. For example, some can be synthesized by modifying commercially available caffeic acid to convert its COOH and/or OH groups to ester or ether groups.

Mitochondrial electron transport chain enhancers and antioxidants, also used to practice in this invention, either are commercially available or can be synthesized by methods well known in the art.

Chemical transformations and protection/deprotection methods used to make the desired compounds are well known in the art. They include, but are not limited to, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Compounds thus synthesized can be further purified by flash column chromatography, high performance liquid chromatography, crystallization, or any other suitable methods.

The compounds mentioned herein contain a non-aromatic double bond. Thus, they can occur as cis- or trans-isomeric forms. All such isomeric forms are contemplated.

A compound of formula (I) and a mitochondrial electron transport chain enhancer (or an antioxidant) can be co-used, e.g., at a ratio of 1-10, to treat neurodegenerative diseases. To practice this treatment, an effective amount of a compound of formula (I) and an effective amount of a mitochondrial electron transport chain enhancer (or an antioxidant) can be administered to a patient as a single premixed formulation. For example, one can premix the two agents to form one composition and administer it to a subject. Alternatively, these two agents can be applied as two separate formulations and administered to a patient at the same time or at different times.

Neurodegenerative disorders are characterized by progressive nervous system dysfunction. Examples include, but are not limited to, Parkinson's disease, Huntington's disease, Alzheimer's disease, amyotrophic lateral sclerosis, Batten disease, multiple sclerosis, stroke, and hearing loss. The term "treating" refers to administering one or more active agents to a subject that has a neurodegenerative disorder, or has a symptom of this disorder, or has a predisposition toward this disorder, with the purpose to cure, heal, alleviate, relieve, alter, remedy, ameliorate, improve, or affect the disorder, the symptoms of the disorder, or the predisposition toward the disorder. The term "an effective amount" refers to the amount (e.g., 0.1-5000 mg/kg) of an agent which is required to interact with another agent to confer synergistic therapeutic effect on the treated subject. It can be determined based on animal and clinical studies. Effective doses will also vary, as recognized by those skilled in the art, depending on the route of administration, the excipient usage, and the optional co-usage with other therapeutic treatments.

A compound of formula (I) and a mitochondrial electron transport chain enhancer (or an antioxidant) can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A carrier in a pharmaceutical composition must be "acceptable" in the sense that it is compatible with active ingredients of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active ingredients. Examples of other carriers include colloidal silicon dioxide, magnesium stearate, cellulose, sodium lauryl sulfate, and D&C Yellow #10.

One can assess the efficacy of a combination of a compound of Formula (I) and a mitochondrial electron transport chain enhancer (or an antioxidant) on treating a neurodegenerative disorder by both in vitro and in vivo assays well known in the art. See, e.g., the bioassay provided below.

Without further elaboration, it is believed that one skilled in the art can, based on the description herein, utilize the present invention to its fullest extent. All publications recited herein are hereby incorporated by reference in their entirety. The following specific examples, which describe biological testing of Coenzyme Q10 and a compound of Formula (I), are, therefore, to be construed as merely illustrative, and not limitative of the remainder of the disclosure in any way whatsoever.

Chemical Synthesis:
Synthesis of Compound 1

Compound 1 was synthesized by reacting caffeic acid with excess phenethyl alcohol in the presence of p-toluene sulfonic acid for an extended period of time. See, e.g., Frunberger et al., Experientia, 1988, 44, 23-232.

Synthesis of Compounds 2-4

300 mg (1.66 mmol) of caffeic acid was dissolved in 3.15 ml DMSO. $K_3PO_4$ (2.00 mmol) was added while stirring. Stirring was continued for 30 minutes. At the end, a solution of 1.70 mmol of benzyl bromide in 1.05 ml DMSO was added slowly within 30 minutes. The resulting reaction mixture was stirred at room temperature for 9 hrs and then at 15° C. for 12 hrs. The reaction mixture was slowly added to 20 ml of ice water while stirring and extracted with ethyl acetate (3×10 ml). The aqueous layer was acidified by dropwise addition of 1.0 M aqueous HCl and extracted with ethyl acetate. The combined organic layers were washed sequentially with 1.0 M HCl (2.5 ml) and saturated sodium chloride solution (3×10 ml), dried over anhydrous $Na_2SO_4$, filtered, and concentrated under reduced pressure. The crude material was purified by silica gel chromatography using petroleum ether/ethyl acetate gradient eluent (from 20:1 to 3:1 V/V) and Compound 2 was obtained at a yield of more than 80%.

Compounds 3 and 4 were prepared in the same manner except that naphthylmethyl bromide and bromopropylbenzene were respectively used, instead of benzyl bromide.

Compound 2: $^1$H NMR (300 MHz, DMSO-$D_6$) δ: 9.63 (s, 1H, OH), 9.16 (s, 1H, OH), 7.53 (d, J=15.6 Hz, 1H, C3-H), 6.75~7.43 (m, 8H, Ar—H), 6.33 (d, J=15.9 Hz, 1H, C2-H), 5.20 (s, 2H, $CH_2$); MS (ESI$^+$): [M+H]$^+$ m/z 271, [M+Na]$^+$ m/z 293; m.p.: 150-151° C.

Compound 3: $^1$H NMR (300 MHz, DMSO-$d_6$) δ: 9.371 (brs, 2H, 2×OH), 7.91~9.94 (m, 4H, Ar—H), 7.55 (d, J=15.9 Hz, 1H, C3-H), 7.50~7.54 (m, 3H, Ar—H), 7.00~7.07 (m, 2H, Ar—H), 6.76 (d, J=8.1 Hz, 1H, Ar—H), 6.36 (d, J=15.9 Hz, 1H, C2-H), 5.35 (s, 2H, $CH_2$); $^{13}$C NMR (75 MHz, DMSO-$d_6$) δ: 166.5, 148.5, 145.7, 145.6, 134.1, 132.8, 132.6, 128.2, 127.9, 127.6, 126.8, 126.4, 126.3, 125.9, 125.5, 121.6, 115.7, 114.9, 113.7, 65.4; MS (ESI$^-$): [M−H]$^-$ m/z 319; m.p.: 172-175° C.

Compound 4: $^1$H NMR 300 MHz, DMSO-$d_6$) δ: 9.21 (brs, 2H, OH), 7.46 (d, J=15.9 Hz, 1H, C3-H), 6.75~7.34 (m, 8H, Ar—H), 6.24 (d, J=15.9 Hz, 1H, C2-H), 4.32 (t, J=6.9 Hz, 2H, COO$CH_2$$CH_2$), 2.95 (t, J=6.9 Hz, 2H, COOCH$_2$$CH_2$); MS (FAB): [M+H]$^+$ m/z 285; m.p.: 102~103° C.

Synthesis of Compounds 5-7

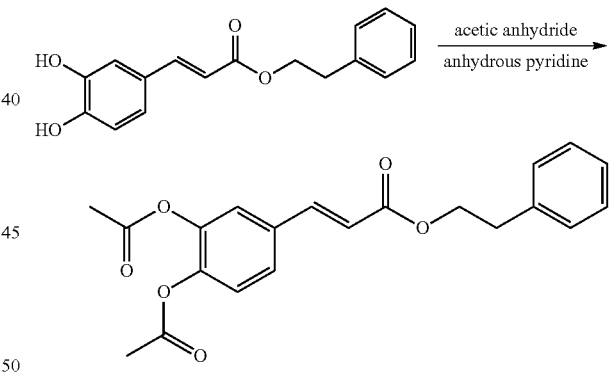

Caffeic acid phenethyl ester (2.5 mmol) was dissoved in 6 ml acetic anhydride, mmol (0.43 ml) anhydrous pyridine was added while stirring. After stirred at room temperature for 5 minutes, the reaction mixture was then slowly added to 30 ml of ice water while stirring and then extracted with ethyl acetate (3×10 ml). The combined organic layers were washed with saturated sodium chloride solution (3×10 ml). The organic layer was dried over anhydrous $MgSO_4$, filtered, and concentrated under reduced pressure. The crude material was purified by silica gel chromatography using of petroleum ether/ethyl acetate gradient eluent (from 20:1 to 8:1 V/V) to give Compound 7 at a yield of 96%.

Compounds 5-8 were prepared by in the same manner except that different starting maters were used.

Compound 5: $^1$H NMR (300 MHz, CDCl$_3$) δ: 7.66 (d, J=15.9 Hz, 1H, C3-H), 7.20~7.40 (m, 8H, Ar—H), 6.43 (d, J=15.9 Hz, C2-H), 5.24 (s, 2H, CH$_2$), 2.29 (s, 6H, 2×CH$_3$); $^{13}$C NMR (75 MHz, CDCl$_3$) δ: 168.0, 167.9, 166.3, 143.5, 143.1, 142.3, 135.8, 133.1, 128.5, 128.2, 126.3, 123.9, 122.7, 119.0, 66.4, 20.6, 20.5; MS ($^+$ESI-TOF): [M+NH$_4$]$^+$ m/z 372, [M+Na]$^+$ m/z 377; m.p.: 101~103° C.

Compound 6: $^1$H NMR (300 MHz, CDCl$_3$) δ: 7.60 (d, J=16.2 Hz, 1H, C3-H), 7.20~7.43 (m, 8H, Ar—H), 6.39 (d, J=15.9 Hz, 1H, C2-H), 4.22 (t, J=6.6 Hz, 2H, phCH$_2$CH$_2$CH$_2$), 2.74 (t, J=7.5 Hz, 2H, phCH$_2$CH$_2$CH$_2$), 2.31 (s, 3H, CH$_3$), 2.30 (s, 3H, CH$_3$), 2.04 (m, 2H, phCH$_2$CH$_2$CH$_2$); $^{13}$C NMR (75 MHz, CDCl$_3$) δ: 168.0, 167.9, 166.5, 143.4, 142.7, 142.4, 141.1, 133.2, 128.5, 126.3, 126.0, 123.9, 123.8, 122.7, 122.6, 119.3, 63.9, 32.2, 30.2, 20.7, 20.5; MS (ESI$^+$): [M+H]$^+$ m/z 383, [M+NH$_4$]$^+$ m/z 400; m.p.: 65~67° C.

Compound 7: $^1$H NMR (300 MHz, CDCl$_3$) δ: 7.60 (d, J=15.9 Hz, 1H, C3-H), 7.20~7.57 (m, 8H, Ar—H), 6.36 (d, J=15.9 Hz, 1H, C2-H), 4.41 (t, J=7.2 Hz, 2H, COOCH$_2$CH$_2$), 3.01 (t, J=7.2 Hz, 2H, COOCH$_2$CH$_2$), 2.30 (6H 2×CH$_3$); $^{13}$C NMR (75 MHz, CDCl$_3$) δ: 168.0, 167.9, 166.4, 143.4, 142.8, 142.4, 137.7, 133.2, 128.9, 128.5, 126.5, 126.4, 123.9, 122.7, 119.2, 65.1, 35.1, 20.6; MS ($^+$ESI-TOF): [M+NH$_4$]$^+$ m/z 369, [M+NH$_4$]$^+$ m/z 386, [M+Na]$^+$ m/z 391, [M+K]$^+$ m/z 407; m.p.: 82~83° C.

Compound 8: $^1$H NMR (300 MHz, CDCl$_3$) δ: 7.66 (d, J=16.2 Hz, 1H, C3-H), 7.21~7.43 (8H, Ar—H), 6.71 (d, J=15.9 Hz, 1H, CH$_2$CH=CH), 6.42 (d, J=15.9 Hz, 1H, C2-H), 6.30~6.38 (m, 1H, CH$_2$CH=CH), 4.87 (d, J=7.5 Hz, 2H, CH$_2$), 2.30 (s, 6H, 2×CH$_3$); $^{13}$C NMR (75 MHz, CDCl$_3$) δ: 168.0, 167.9, 166.3, 143.5, 143.1, 142.4, 136.1, 134.3, 133.2, 128.6, 128.0, 126.6, 123.9, 123.8, 123.0, 122.8, 122.6, 119.0, 65.2, 20.6, 20.5); MS ($^+$ESI-TOF): [M+NH$_4$]$^+$ m/z 398, [M+Na]$^+$ m/z 403; m.p.: 86~88° C.

Bioassay:

Compound 1 was dissolved in a PEG solvent (30% PEG 400, 5% EtOH, 5% DMSO, 1 mg/ml). The solution was mixed with Coenzyme Q10 in liposome (5 mg/ml, NuNaturals).

Mice that over-expressed human Cu,Zn superoxide dismutase-1 mutant G93A to develop a delayed and progressive motor neuron disease similar to human amyotrophic lateral sclerosis (ALS) were used in this assay.

The mixture of Compound 1 and Coenzyme Q10 were administered by gavage (oral) once a day (final dosage: 10 mg/kg of Compound 1 and 50 mg/kg of Coenzyme Q10) to 5 mice. The average survival time for the mice was 156 days.

As control, mice were subject to Compound 1 treatment, Coenzyme Q10 treatment, or no Compound 1 or Coenzyme Q10 treatment. The average survival time was 138 days for Compound 1-treated mice, 129 days for Coenzyme Q10 treatment mice, and 125 days for no Compound 1 or Coenzyme Q10-treated mice.

These results show that a combination of Compound 1 and Coenzyme Q10 significantly enhanced neuroprotective effect, compared with Compound 1 or Coenzyme Q10 alone.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical composition, comprising a mixture of a mitochondrial electron transport chain enhancer or an antioxidant and a compound selected from the group consisting of

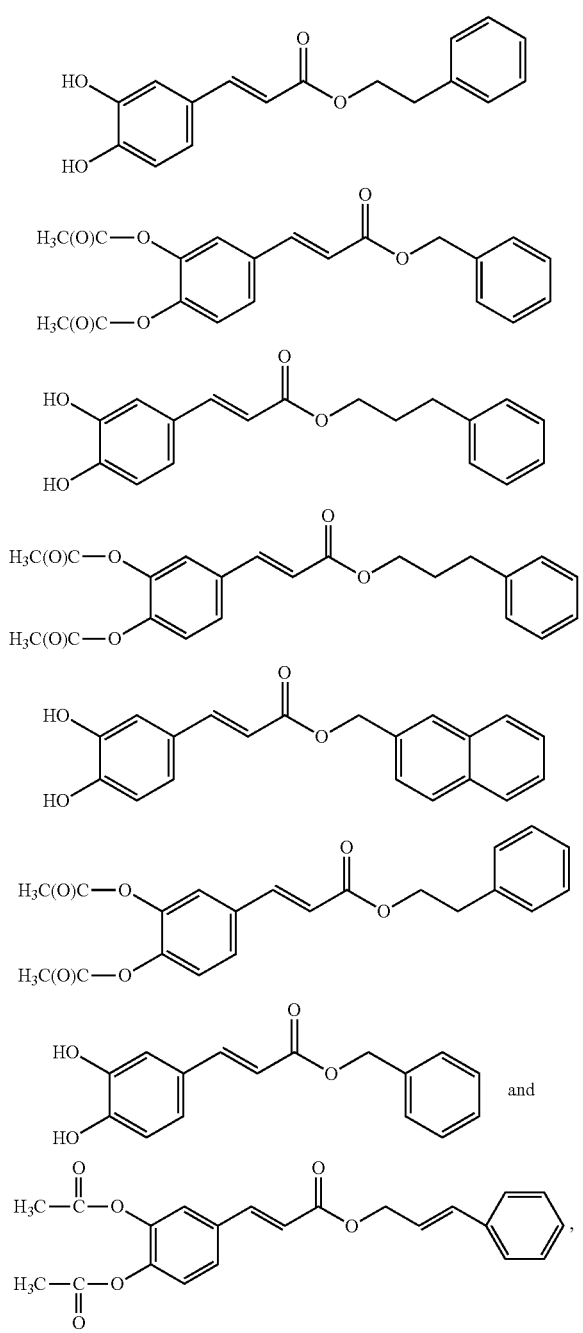

the mitochondrial electron transport chain enhancer or the antioxidant being Coenzyme Q10.

2. The pharmaceutical composition of claim 1, wherein the compound is

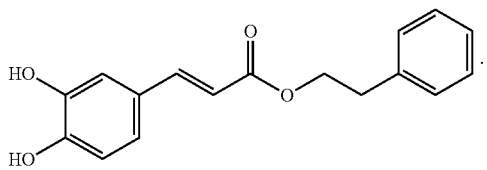 [SMILES: O=C(/C=C/c1ccc(O)c(O)c1)OCCc1ccccc1]

3. A method of treating a neurodegenerative disorder, comprising administering to a subject in need thereof a mixture of an effective amount of a mitochondrial electron transport chain enhancer or an antioxidant and an effective amount of a compound selected from the group consisting of

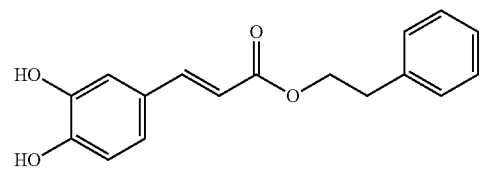

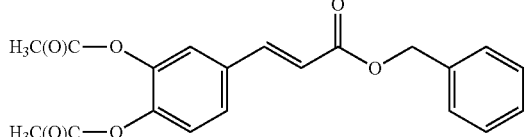

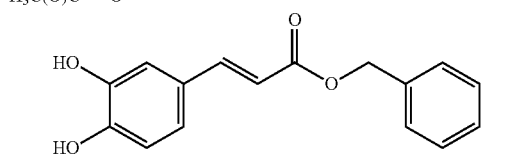

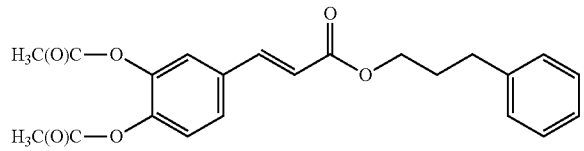

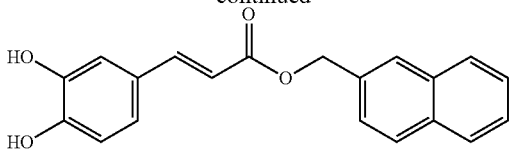

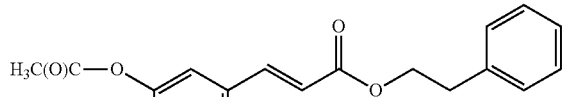

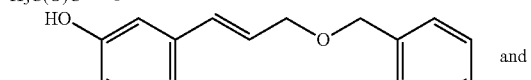

and

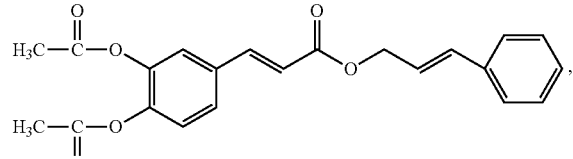

the mitochondrial electron transport chain enhancer or the antioxidant being Coenzyme Q10 wherein the neurodegenerative disorder is amyotrophic lateral sclerosis.

4. The method of claim 3, wherein the compound is

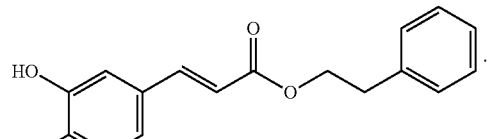

* * * * *